United States Patent [19]

Narayanan et al.

[11] Patent Number: 4,599,352

[45] Date of Patent: Jul. 8, 1986

[54] ANTINEOPLASTIC PLATINUM (IV) COMPLEXES AND COMPOSITIONS

[75] Inventors: Venkatachala L. Narayanan, Gaithersburg; Mary K. Wolpert-Defilippes; Rudiger D. Haugwitz, both of Bethesda, all of Md.

[73] Assignee: The United States of America as represented by the Department of Health and Human Services, Washington, D.C.

[21] Appl. No.: 585,111

[22] Filed: Mar. 1, 1984

[51] Int. Cl.$^4$ .................... A01N 55/02; A61K 31/28; C07F 15/00
[52] U.S. Cl. .................... 514/492; 556/137
[58] Field of Search ............ 260/429 R; 424/287; 556/137; 514/492

[56] References Cited

U.S. PATENT DOCUMENTS 4,177,263 12/1979 Rosenberg et al. ............ 424/131
4,200,583 4/1980 Kidani et al. ............ 260/429 R X
4,431,666 2/1984 Bulten et al. ............ 260/429 R
4,466,924 8/1984 Verbeek et al. ............ 260/429 R
4,482,569 11/1984 Bulten et al. ............ 260/429 R

FOREIGN PATENT DOCUMENTS 8000032 8/1981 Netherlands .
2060615A 5/1981 United Kingdom ............ 260/429 R

OTHER PUBLICATIONS

Braddock, et al., Chem. Biol. Interactions (Amsterdam), vol. 11, No. 3, 1975.
Chemical Abstracts 83 125415j (1975).
Chemical Abstracts 78 115716r (1973).
Chemical Abstracts 74 57866u (1971).
Nature, V222, pp. 385–386 (1969).
J.A.C.S. 95(6), pp. 2047–2048 (1973).
Chemical Abstracts 86 182963x.
Hall et al., Wadley Med. Bull. 7:231 (1977).
Schwartz et al., Cancer Treatment Reports 61:1519 (1977).

Primary Examiner—Helen M. S. Sneed
Attorney, Agent, or Firm—Holman & Stern

[57] ABSTRACT

New substantially isomerically pure tetrahalo (1,2-diaminocyclohexane) Pt (IV) complexes having antineoplastic activity are disclosed.

13 Claims, 1 Drawing Figure

ANTINEOPLASTIC PLATINUM (IV) COMPLEXES AND COMPOSITIONS

BACKGROUND OF THE INVENTION

1. Technical Field

The present invention is directed to novel platinum (IV) complexes having antitumor or antineoplastic activity. More particularly, the present invention relates to substantially isomerically pure tetrahalo, preferably tetrachloro, (1,2-diaminocyclohexane) platinum (IV) compounds and their use as effective antitumor agents.

2. Description of the Prior Art

Various platinum coordination compounds and their use as antitumor agents are known. Rosenberg et al (U.S. Pat. No. 4,177,263) discloses several platinum complexes and a method of treating malignant tumors by the parenteral administration of platinum complexes including a cis-tetrachlorodiammine platinum (IV) complex. Belgium Pat. No. 886,929 (Chem. Abstracts 95, 181, 198a) discloses di- and tetrahalo (1,1-diaminomethylcycloalkane) Pt (II) and Pt (IV) compounds as antitumor agents. German Offen. DE No. 3,207,472 discloses cis-dichloro trans-dihydroxy [1-amino-2-(aminomethyl)-3,3,5-trimethylcyclopentane]-platinum (IV) and related structures for the treatment of cancer. U.S. Pat. No. 360,424 and German Pat. No. 158,777 describe organoplatinum complexes and their preparation. U.S. Pat. No. 4,200,583 discloses cis-platinum (II) coordinates 1,2-diaminocyclohexane (cis-, trans-l and trans-d) exhibiting anti-tumor activity. Hill et al, Anticancer Research 2, 173, (1982), presents a recent review of organoplatinum complexes as antitumor agents. Schwartz et al, Cancer Treatment Reports, 61, 1519 (1977), discloses the synthesis, water solubility and antileukemic activity of tetrachloro (1,2-diaminocyclohexane) platinum (IV) complex (NSC 276017). It should be noted, however, that the Pt(IV) complex of Schwartz et al, supra, designated NSC 276017, is an isomeric mixture [cis and trans (d and l)] of the tetrachloro (1,2-diaminocyclohexane) platinum (IV) complex and not an isomerically pure preparation. Furthermore, as noted by Hall et al, Wadley med. Bulletin, 7 (1):231 (1977), wherein studies relating to antileukemic activity of several platinum (IV) analogs including a tetrachloro (1,2-diaminocyclohexane) derivative have been described, "platinum (IV) compounds were, in general, less active than the corresponding platinum (II) species". Since Hall et al, supra, clearly states that "All diamines are in the 'trans' configuration", it is clear that the compounds tested by Hall et al, supra, are not isomerically pure complexes but a mixture of optical isomers, possibly cis. In any event, an isomerically pure preparation of Pt(IV) complex could not have been the object of Hall et al's study since methods to detect an isomeric mixture simply did not exist at that time. Furthermore, Hall et al reached the conclusion that "- - - the activity of most platinum II analogs were lowered by oxidation to a plus four state".

It may be noted in this connection that Kidani et al., Gann, 67, 921, (1976) reported differences in antitumor activity (leukemia L1210) when testing pure isomers of dichloro (1,2-diaminocyclohexane) platinum (II) complex: the trans (l) isomer showing the highest activity, the trans (d) isomer possessing intermediate activity while the cis was the least active.

Later, the same authors reported on the antitumor activity (sarcoma-180, ascites form) for the same compounds and stated that in this test-system the cis isomer was more efficacious than the corresponding trans isomers. See J. Med. Chem., 21: 1315, (1978). Observation on these and related compounds can be found summarized in *Structure-Activity Relationships of Antitumor Agents*, 59 (1983).

In light of the generally held view among those skilled in the art that Pt(IV) analogs exhibit relatively poor antineoplastic activity compared to Pt(II) coordination compounds, the focus of research and screening of anti-cancer drugs has centered mostly in the development of Pt(II) complexes. In fact, the remarkable success of cisplatin, cis-diamminedichloroplatinum (II), as an efficacious drug in the treatment of testicular and other cancers has given impetus to the testing of a wide variety of organoplatinum compounds, particularly of the Pt (II) variety.

It should be noted, however, that the usefulness of cisplatin has been limited by its lack of effectiveness against cisplatin-resistant tumor cells and due to its toxicities, mainly nephrotoxicity, nausea and vomiting, myelosuppression, ototoxicity, peripheral neuropathy, allergic reactions, and electrolyte imbalances, including hypomagnesia. Because of these limitations, there has been a concerted effort to develop platinum complexes generally having the following properties: comparable or superior activity to cisplatin in a variety of experimental tumor models, lack of cross-resistance with cisplatin, lesser toxicity than cisplatin, good water solubility, good stability in aqueous solution, good purity and chemical homogeneity. As noted herein above, the development of Pt(IV) complexes generally had been ignored because of early work by Hall et al, supra, and others concluding that Platinum IV complexes were usually less active than their corresponding Platinum II complexes. Furthermore, one of the most recalcitrant problems in the clinical treatment of cancer is the problem of drug resistance. A physician needs to be able to switch from one drug or combination of drugs to another drug (or combination of drugs) to eradicate cells which no longer respond to the first treatment. Based on the well-accepted hypothesis of tumor cell heterogeneity, it is not unexpected that the initial treatment may produce a clinical response by killing a select population of sensitive cells. However, if the tumor is not completely eradicated, it is quite possible for tumor cells with reduced sensitivity to the original treatment to repopulate the tumor. In such circumstances the use of other treatment modalities, e.g. other chemotherapeutic agents, radiation therapy and the like, is usually necessary.

The Applicants have now surprisingly discovered that certain substantially isomerically pure Pt (IV) complexes not only have potent regressive activity against malignant tumors but also have efficacy against a subline of tumor cells with acquired resistance to cisplatin.

SUMMARY OF THE INVENTION

It is therefore, an object of the present invention to provide a new group of Pt(IV) derivatives having substantially different spectrum of antineoplastic activity.

It is another object of the present invention to provide substantially isomerically pure organoplatinum (IV) complex having antitumor activity.

A further object of the present invention is to provide substantially isomerically pure tetrahalo, preferably tetrachloro, (1,2-diaminocyclohexane) platinum (IV) compounds useful as antitumor agents.

A still further object of the present invention is to provide a method of treating malignant tumor cells sensitive to substantially isomerically pure tetrahalo (1,2-diaminocyclohexane) platinum (IV) compound in mammals including humans which comprises administering to a mammal afflicted with said tumor cells an effective amount of said platinum (IV) compound to cause regression of said tumor cells.

Another object of the present invention is to provide a pharmaceutical composition for the treatment of malignant tumors in a mammalian host comprising a sufficient amount of a substantially isomerically pure tetrahalo (1,2-diaminocyclohexane) platinum (IV) compound as an active ingredient to treat said malignant tumors.

Other objects and advantages will appear as the description of the invention proceeds.

DETAILED DESCRIPTION OF THE INVENTION

Figure 1:
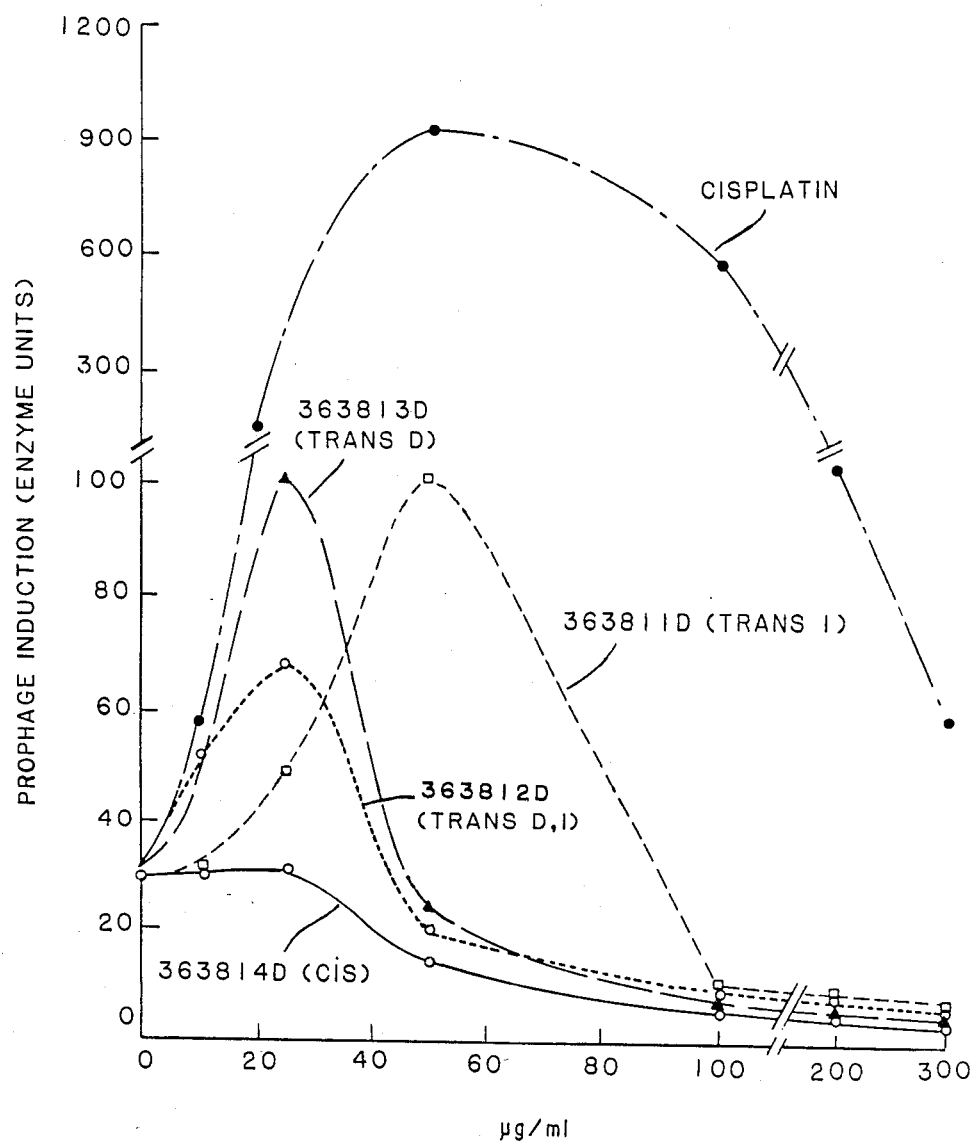

These and other objects, features and many of the attendant advantages of the present invention will be better understood upon a reading of the following detailed description when considered in connection with the accompanying FIG. 1 which is a graphical representation of the activity of platinum complexes in the biochemical phage induction assay.

The attainment of various objects and advantages of the present invention is made possible by the compounds, methods and compositions comprising a substantially isomerically pure tetrahalo (1,2-diaminocyclohexane) platinum (IV) complex of the following formula:

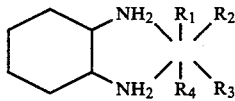

wherein $R_1$, $R_2$ $R_3$ and $R_4$ are the same or different substituents selected from the group consisting of chlorine, bromine, iodine and fluorine.

The term substantially pure designates that the compound has less than 10% impurity, preferably less than 5% impurity and more preferably less than 1% impurity.

Some of the unexpected properties of said Pt (IV) complex of the present invention are as follows:

(1) The compound of the present invention is effective against several lines of malignant tumors including cisplatin-resistant tumor cells.

(2) The analogs of the present invention are more water soluble than the mixture of their isomers.

(3) The compounds of the present invention are relatively less toxic than cisplatin.

(4) The compounds of the present invention have outstanding hydrolytic stability.

(5) The organoplatinum complex of the present invention can be lyophilized and sterilized without any detrimental effect in their property; and (6) Because of the substantial purity of the compounds of the present invention, their chemical definition, analysis, dosage regimen, batch to batch reproducibility, stability-indicating assay and other characteristics are easily determinable and verifiable.

The applicants are the first to discover the compounds disclosed by the present invention which possess an aggregate of such novel, useful and superior properties as enumerated herein above.

The platinum (IV) complexes of the present invention can be prepared by a number of classical methods which should be well known to those skilled in the art to which it pertains. One of the methods is to react a substantially isomerically pure 1,2-diaminocyclohexane with $K_2PtCl_4$ to obtain an analogous intermediate Pt (II) complex and then react resulting Pt(II) complex with a halogen to obtain the Pt(IV) compound of formula 1. The parameters of the synthetic processes which can be utilized to obtain the compound of the present invention have been described, inter alia, by Kidani et al. Chem. Letter, 123: (1976) and in Tumori, 69:31, (1983) both of which are incorporated herein by reference.

The best mode of preparing the compounds of the present invention, which mode per se is not a part of the invention claimed herein, is the process of Anderson et al of the State University of New York at Buffalo and has been described herein infra. However, as noted herein above, other methods of preparing the compounds of the present invention can also be advantageously employed.

The following examples more fully illustrate the preferred embodiments including various intermediates or products and methods which can be employed in the preparation of the Pt (IV) complexes of the present invention.

Separation of cis- and trans-1,2-diaminocyclohexane

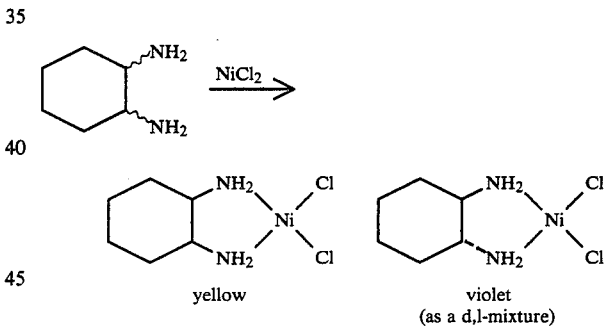

yellow      violet (as a d,l-mixture)

A solution of 1,2-diaminocyclohexane (50.0 g; 0.44 mol) in methanol (200 ml) is added over a period of 2 min to a stirred solution of $NiCl_2.6H_2O$ (52.0 g; 0.22 mol) in methanol (500 ml). The initial light green solution turns dark blue-green after the diamine is added and a solid precipitate appears in 20 min. The mixture is stirred for 3 h then vacuum filtered to leave a yellow-green solid and a violet-blue filtrate. The solid is stirred in methanol (2×300 ml) for 2 h, vacuum filtered, and washed with methanol. The solid is dried, first in vacuo to remove traces of methanol then in a vacuum desiccator ($P_2O_5$) to yield 25.5 g of the yellow cis-1,2-diaminocyclohexane complex.

The violet-blue filtrate obtained above is acidified with 6N HCl (60 ml) then the pH is adjusted to 4.2–4.5 with 20% aqueous NaOH. Violet crystals of the trans-1,2-diaminocyclohexane complex are deposited overnight. The crystals are filtered, washed with water and dried in a vacuum desiccator ($P_2O_5$) to give 29.0 g of a violet solid.

Reference: Kidani, Y.; Saito, R. *Chem. Lett.* 1976, 123.

Cis-1,2-diaminocyclohexane

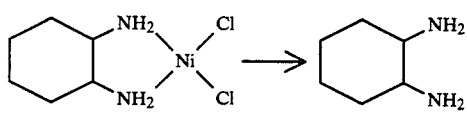

The yellow cis-1,2-diaminocyclohexanedichloronickel(II) (20 g) is added portionwise to stirred 6N H$_2$SO$_4$ (250 ml) over a period of 20 min. After 1 hour, the water is removed in vacuo to leave a viscous green oil. Absolute ethanol (160 ml) is added to the oil to produce a white solid. The solid is vacuum filtered, washed with absolute ethanol and dried in vacuum desiccator (P$_2$O$_5$) to give 20.0 g of white solid cis-1,2-diaminocyclohexane hydro-sulfate.

The cis-1,2-diaminocyclohexane hydrosulfate (8.0 g; 0.033 mol) is added to 15% aqueous NaOH (60 ml) and continuously extracted with benzene for 8 h. The benzene is dried (K$_2$CO$_3$), filtered and evaporated in vacuo to leave 3.44 g (92%) of cis-1,2-diaminocyclohexane as a colorless oil: IR (neat) 3362(s), 3288(s), 2942 (s), 2856(s), 1592 (s), 1445 (s), and 846 (s) cm$^{-1}$; $^1$H-nmr (CDCl$_3$/TMS) 2.88 (2$\underline{H}$,br), 1.50 (4$\underline{H}$,br), 1.17 (4$\underline{H}$,s); $^{13}$C-nmr (d-DMSO/TMS) 51.92, 30.74, and 21.93.

Trans-(d,l)-1,2-diaminocyclohexane

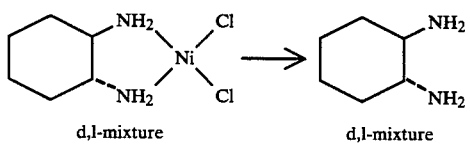

This diamine is prepared in 76% yield by the same procedure used for the cis-diamine except the violet trans-(d,l)-1,2-diaminocyclohexane-dichloronickel (II) is used. IR (neat) 3355(s), 3282 (s), 2942 (s), 1585 (s), 1445 (s), 953 (s), 893 (s), 866 (s), and 680 (s) cm$^{-1}$; $^1$H-nmr (CDCl$_3$/TMS) 2.45–2.10 (2$\underline{H}$,br), 2.10–1.50 (4$\underline{H}$,br), and 1.30 (4$\underline{H}$,s).

(1S, 2S), Trans-(d)-1,2-diaminocyclohexane

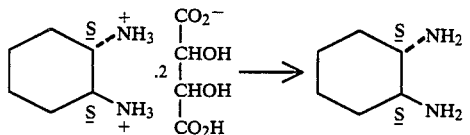

This optically active diamine is prepared in 72% yield by the method described for the conversion of cis-1,2-diaminocyclohexane hydro-sulfate to cis-1,2-diaminocyclohexane except that trans-(d)-1,2-diaminocyclohexane ditartrate is used. $[\alpha]_{589}^{25} = +33.7°$ (c=5; benzene).

(1R,2R)-Trans-(l)-1,2-Diaminocyclohexane

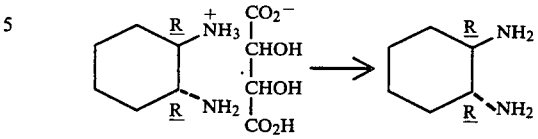

This optically active diamine is prepared in 70% yield by the method described for the synthesis of the trans-(d)-isomer except that trans-(l)-1,2-diaminocyclohexane tartrate is used. $[\alpha]_{589}^{25} = -35.1°$ (c=5; benzene); lit. $[\alpha]_{589}^{25} = -36.0°$ (Whitney, T. A. *J. Org. Chem.* 1980, 45, 4214).

Cis-dichloro-cis-1,2-cyclohexanediamine platinum (II)

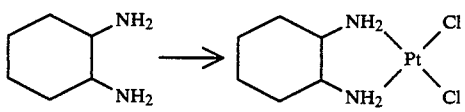

A mixture of cis-1,2-diaminocyclohexane (0.684 g; 6.0 mmol) and degassed water (5 ml; degassed by vacuum purging) is added to a stirred solution of potassium tetrachloro-platinate (II) (2.50 g; 6.0 mmol) in degassed water (25 ml) maintained under a blanket of nitrogen gas. The mixture is stirred for 18 h then vacuum filtered. The solid is washed with IN HCl, ethanol, and finally with diethyl ether. The air-dried material is a pale yellow solid (2.24 g; 98% yield). The solid is dissolved in DMF, the mixture is filtered, and methanol is added to precipitate the cis-dichloro-cis-1,2-cyclohexanediammine platinum (II); IR (KBr) 3253 (s), 3118 (s), 2945 (s), 2862 (s), 1569 (s), 1445 (s), 1196 (s), 980 (s), and 762 cm$^{-1}$(s).

The compound has very low solubility in water and methanol; it dissolves 50 mg/ml in DMF.

Reference: Kidani, et al *J. Med. Chem.* 1978, 21, 1315.

Cis-dichloro-trans-(d,l)-1,2-cyclohexanediamine platinum (II)

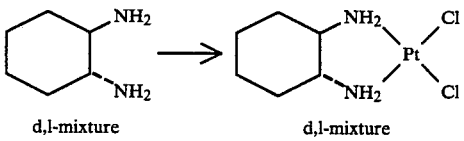

This compound is prepared in 95% yield with the same procedure used for the synthesis of cis-dichloro-cis-1,2-cyclohexanediammine platinum (II) except that trans-(d,l)-1,2-cyclohexanediamine is used. Ir (KBr) 3274 (s), 3193 (s), 2934 (s), 2866 (s), 1564 (s), 1160 (s), and 756 cm$^{-1}$ (s).

The compound has very low solubility in water and methanol; it dissolves in DMF 50 mg/ml.

Anal. Calcd for C$_6$H$_{14}$N$_2$Cl$_2$Pt: C, 18.96; H, 3.71; N, 7.37, Cl, 18.66. Found: C, 19.10; H, 3.71; N, 7.35; Cl, 18.71.

Cis-dichloro-trans-(1R,2)-1,2-cyclohexanediamine platinum (II)

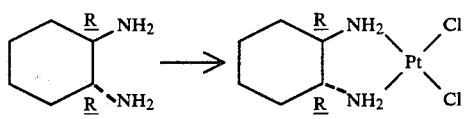

This compound is prepared by the same method used to synthesize the racemic (d,l)-mixture except that trans-(1R,2R)-1,2-cyclohexanediamine is used.

Cis-cichloro-trans-(1S,2S)-1,2-cyclohexanediamine platinum (II)

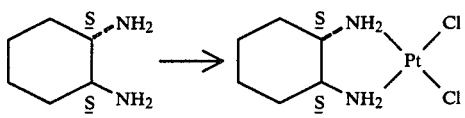

This compound is prepared by the same method used to synthesize the racemic (d,l)-mixture except that trans-1S,2S)-1,2-cyclohexanediamine is used.

Tetrachloro-cis-1,2-cyclohexanediamine platinum (IV)

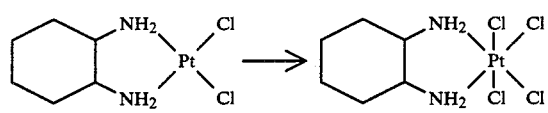

This compound is prepared by the same procedure used for the synthesis of the trans-(d,l) complex except that cis-dichloro-cis-1,2-cyclohexanediammine platinum (11) is used. Ir (KBr) 3185 (s), 3090 (s), 2938 (s), 2865 (m), 1560 (s), 1451 (m), 1202 (s), 1131 (m), 976 (m), and 583 (m) cm$^{-1}$; $^{13}$C-nmr (d$^7$-DMF/TMS) 60.90, 26.30, and 21.72.

The compound is soluble <10 mg/ml in water, 50 mg/ml in methanol, 200 mg/ml methanol-acetone (1:1), and 250 mg/ml in DMF.

Anal. Calcd for C$_6$H$_{14}$N$_2$Cl$_4$Pt: C, 15.98; H, 3.13; N, 6.21; Cl, 31.44, Found: C, 16.25; H, 3.20; N, 6.09; Cl, 31.17.

(d,l)-Tetrachloro-trans-1,2-cyclohexanediamine platinum (IV)

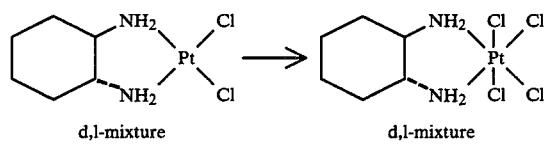

d,l-mixture    d,l-mixture

Chlorine gas is bubbled at a rate of 2 bubbles per second under the liquid surface of a stirred suspension of cis-dichloro-trans-(d,l)-1,2-cyclohexanediamine platinum (11) (2.10 g; 5.5 mmol) in 0.5N HCl (40 ml) at 60° C. The temperature is raised to 100° C. as soon as the chlorine is introduced. The solid turns red-orange in color then to a bright yellow with a portion dissolving. Chlorine is bubbled into the mixture for 2.5 h then air is rapidly bubbled through the mixture to displace unreacted chlorine. The cooled reaction mixture is evaporated to dryness in vacuo, methanol (250 ml) is added to the yellow residue and the mixture is filtered. The filtrate is evaporated to dryness in vacuo to yield 2.14 g (87%) of a bright yellow solid: ir (KBr) 3228 (s), 3180 (s), 3090 (s), 2942 (s), 2863 (s), 1566 (s). 0.1450 (m), 1166 (s), 1060 (s), and 917 (m) cm$^{-1}$; $^1$H-nmr (d$^7$-DMF/TMS)δ8.1–7.0 (br), 3.6 (br), 3.3 (s), 3.1 (br), 2.2(br), 1.5(br), and 0.7(s); $^{13}$C-nmr (d$^7$-DMF/TMS)δ63.96, 31.82, and 24.56.

The compound is soluble <10 mg/ml in water, 100 mg/ml in methanol, and 250 mg/ml in DMF.

(1S, 2S)-Tetrachloro-trans-1,2-cyclohexanediamine platinum (IV)

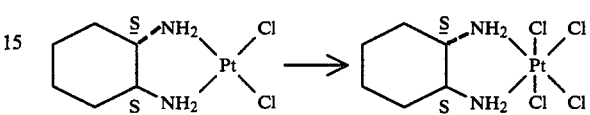

This compound is prepared by the procedure used to prepare the (d,l)-complex except (1S,2S)-cis-dichloro-trans-1,2-cyclohexanediammine platinum (11) is used. [α]$_{589}^{25}$ = −129.13° (c=3.33, methanol).

Anal. Calcd for C$_6$H$_{14}$N$_2$Cl$_4$Pt: C, 15.98; H, 3.13; N, 6.21. Found: C, 16.01; H, 3.13; N, 6.12.

(1R,2R)-Tetrachloro-trans-1,2-cyclohexanediammine platinum (IV)

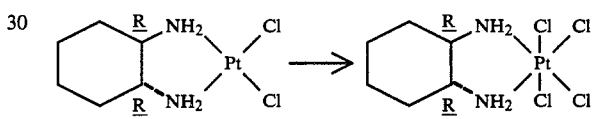

This compound is prepared by the procedure used to prepare the (d,l)-complex except (1R,2R)-cis-dichloro-trans-1,2-cyclohexanediammine platinum (11) is used. [α]$_{589}^{25}$ = +129.73° (c=3.33, methanol).

Anal. Calcd for C$_6$H$_{14}$N$_2$Cl$_4$Pt: C, 15.98; H, 3.13; N, 6.21; Cl, 31.44. Found: C, 16.06; H, 3.15; N, 6.20; Cl, 31.49.

ANALYTICAL PROCEDURES

Analysis of the preparations made according to the procedure described herein above can be obtained using well known techniques such as mass spectrometry, nuclear magnetic resonance (NMR), infrared and UV spectroscopy, high pressure liquid chromatography, optical rotation, radioactive isotope analysis and the like. Some of these techniques employed herein are described below.

Infrared Spectroscopy as a Method to Determine the Amount of Pt (II) Present in Samples of Pt (IV)

A very strong rocking absorption, of the amino group at 756 cm$^{-1}$ in the cis-dichloro-trans-1,2-cyclohexanediamine platinum (11) is absent in the spectrum of the corresponding platinum (IV) compound. Application of the Beer-Lambert laws shows that there is less than 1% of platinum (II) in the sample of (d,l)-tetrachloro-trans-1,2-cyclohexanediamine platinum (IV). Similar analyses of the spectra of the 1S,2S- and 1R,2R-isomers shows comparable purity.

The strong rocking triplet absorption centers at 761 cm$^{-1}$ in the cis-dichloro-cis-1,2-cyclohexanediamine platinum (II) is absent in the corresponding Pt (IV) compound. Again, less than 1% of Pt (II) is present in the sample of tetrachloro-cis-1,2-cyclohexanediamine platinum (IV).

High Pressure Liquid Chromatography (HPLC)

The HPLC studies are carried out using a Spectra Physics SP8000 equipped with a Varian Varichrome variable wavelength detector. The injection volumes are 10 μL, injection concentrations are 1-2 mg/ml, flow rates are 1-2 ml/min. The UV detector is set to monitor 300 nm. Two different systems are used. These are a C8, reversed phase (25 cm×4.6 mm) column eluted with either DMF or methanol and, second, cation-anion exchange columns (each 25 cm×4.6 mm) connected in tandem and eluted with a DMF-aqueous acetate buffer (9:1).

All compounds injected are shown to be greater than 99% pure by each of the above systems. Separation of the Pt (II) and Pt (IV) compounds is not achieved with either system. The extinction coefficient of Pt (II) is much lower than the extinction coefficient of Pt (IV), (0.1 $\epsilon$Pt (IV) ~ $\epsilon$Pt (II)).

BIOLOGICAL PROPERTIES

Biological properties of the compounds of the present invention were determined following the protocol described in *Cancer Chemotherapy Reports*, Vol. 3, No. 3, 1972 which report is incorporated herein by reference. Specific details of particular experiments are those as shown in the Tables, intra.

PHAGE INDUCTION ASSAY

The platinum complexes are tested using the BIA quantitative tube assay for dose-dependent induction of bacteriophage lambda according to a previously published procedure of Sarma, D. et al. *Chem. Biol. Interactions*, 46: 219-232 (1983), which is incorporated herein by reference. A permeable strain of *E. coli* (BR 513) containing lambda phage is used to test all samples. Expression time for the assay is 5 hours at 38° C. Fresh dilutions of test samples are made in saline (0.85%) on the day of the experiment. Samples are made at 10×final concentration and dispensed according to assay procedure. Final concentrations are 300 μg/ml, 200 μg/ml, 100 μg/ml, 60 μg/ml, 25 μg/ml, 10 μg/ml and a zero control.

This strain of bacteria contains a chromosomally integrated lambda-lac Z fusion phage under control of the lambda repressor. Treatment with DNA-damaging agents leads to derepression of prophage and synthesis of β-galacto-sidase, product of the lac Z gene. β-galactosidase is detected by reaction with a substrate (O-nitrophenyl-D-galactopyranoside (ONPG)) to give a yellow-colored product. Tubes are incubated at 28° C. (a few minutes to several hours to an $A_{420} \approx 0.5-1.0$). Color development is stopped by the addition of base (1M $Na_2CO_3$), and the yellow color is measured by absorbance at 420 nm. The exact time required for color development is recorded. Enzyme Units = 100 $A_{420}/t_{hr}$ where $A_{420}$=absorbance at 420 nm; $t_{hr}$=time required to develop yellow color in hours. One enzyme unit is the approximate value of an uninduced control tube at zero time.

PROPERTIES

The results of several studies conducted to test various properties of the compounds of the present invention are presented below.

The isomers of tetrachloro-1,2-cyclohexanediamine platinum (IV), namely trans (l), trans (d, l), trans (d), and cis, are the first to display the desired biological property including activity against a subline of L1210 with acquired resistance to cisplatin and the desired chemical properties including defined chemical structure, adequate solubility, stability, and purity. Also, these are the first complexes with the desired biological property which are also amenable to analyses by several techniques: combustion analysis; high pressure liquid chromatography HPLC; IR spectroscopy; Raman spectroscopy; UV spectroscopy; optical rotation; NMR: proton, carbon-13, or platinum 195; and fast atom bombardment mass spectrometry. Analytical techniques verify the structure and insure that there is no significant batch to batch variation when the compounds of the present invention are prepared for large-scale use. Finally, these isomers are the first to be discovered to date for which the stability is sufficient for the lyophiliziation and sterilization procedures commonly used in developing products for parenteral use, the preferred route of treatment for anticancer agents. Of course, other modes of treatment, e.g. oral, topical, subcutaneous, intramuscular and the like can also be employed.

Of course, the Pt (IV) compounds of the present invention could be administered in any form, e.g. solid, liquid, paste, suspension, solution and the like and in any type of formulation suitable for use in a mammalian host including humans, e.g. tablets, injectable liquids, capsules, granules, oral suspensions and the like. It may also be used in a graft or graft-like form. Any suitable vehicle or carrier may also be employed in the preparation or administering of the formulation of these Pt (IV) compounds. Other additives, agents or adjuvants compatible and/or physiologically acceptable could also be admixed with the Pt (IV) compounds in devising or preparing useful formulations thereof. Some examples of such vehicles, carriers, additives, agents and adjuvants which are otherwise commonly known in the art are saline or buffered solutions; aqueous or non-aqueous dispersions, emulsions or suspensions; fillers; preservatives; stabilizers, emolients and the like.

Table 1 shows the water solubility and purity of the resolved isomers of Pt (IV) complex of the present invention.

TABLE I

| | Water Solubility and Purity | | |
|---|---|---|---|
| | Approximate Solubility | | |
| Isomer | mg/ml | % | Purity (HPLC, IR) |
| trans (l) | 15 | 1.5 | >99% |
| trans (d, l) | 6 | 0.6 | >99% |
| trans (d) | 15 | 1.5 | >99% |
| cis (meso) | 2 | 0.2 | >99% |

As mentioned above, the isomers of tetrachloro-1,2-cyclohexanediamine platinum (IV) are the first to display the desired biological property (activity against a subline of L1210 with acquired resistance to cisplatin and the desired chemical properties, i.e. defined chemical structure and adequate solubility, stability and purity for pharmaceutical development. Table 2 shows a typical dose-response study in the intraperitoneally (IP) implanted L1210 leukemia model. The four isomers are directly compared, i.e., in the same experiment under the same experimental conditions with cisplatin and carboxyphthalatocyclohexanediamine platinum (II) as positive control reference compounds. These results show that all four isomers produce the same approximate log reduction in tumor cell burden at the end of therapy as cisplatin ($-5.7$ $\log_{10}$ reduction). It should be noted that this reduction of tumor cell burden is produced with less toxicity than with cisplatin as measured by body weight differences between drug treated and diluent control animals. These results are in good agreement with the statement of Rotondo et al that platinum (IV) complexes are generally less toxic than platinum (II) complexes because of their chemical inertness (Rotondo et al, Tumori 69: 31–36 (1983). For example, according to the data in Table 2, the weight difference between cisplatin-treated animals at the dose producing the best therapeutic response (20 mg/kg/injection on a day 1, 5 and 9 schedule) and control animals average $-5.0$ grams. The corresponding data for the isomers average a weight difference of less than $-4$ grams at their optimal doses (8 mg/kg/injection for trans l, trans dl, and trans d, and 16 mg/kg/injection for cis). In this experiment carboxyphthalato cyclohexanediamine platinum (II) produces a $-5.7$ $\log_{10}$ reduction in tumor cell burden at three doses (50, 25, and 12.5 mg/kg/injection); however, the weight difference averages more than $-4$ grams at the top dose.

Table 3 shows a comparative study of the same six complexes against the parent line of L1210 and a subline L1210/cisplatin (3DP31) with acquired resistance to cisplatin. The mechanism of the resistance has yet to be elucidated; however, it has been suggested that it may be an uptake mutant or have a different DNA repair mechanism. Other known mechanisms of resistance for other classes of agents, such as gene amplification or target enzyme change or amplication, also need to be explored. The experiments summarized in Table 3 were conducted at the same time against both sublines using the same drug preparations. The data illustrates that L1210/cisplatin is refractory to cisplatin; however, all four isomers of the present invention and NSC-271674 produce a reduction in tumor buden of at least $-5.9$ logs over the course of therapy. Furthermore, all produce three or more 30-day survivors (final evaluation day of the experiment) at tolerated doses. These experiments were repeated in a second laboratory as documented in Table 4. However, in these experiments the animals were held for 60 rather than 30 days to evaluate whether or not long-term survivors are produced after drug treatment in a more challenging setting. As indicated in Table 4, the finding that cisplatin is active against the parent line of L1210 is reaffirmed (T/C of 240% at an optimal dose of 5 mg/kg/injection on a days 1, 5 and 9 schedule). The lack of activity of cisplatin against L1210/cisplatin is also confirmed. Except for the cis isomer, all the remaining compounds produce three or more 60-day survivors at tolerated doses when tested against L1210/cisplatin. The cis isomer produces only one long term survivor in this experiment.

In another type of experiment the same platinum complexes were directly compared against the SC implanted L1210 following intravenous administration (Table 5). In this assay all the compounds show minimal and equivalent activity. Median % T/C values greater than 150%. i.e. a level indicating significant activity according to statistical analyses performed at the National Cancer Institute are accompanied in these experiments by unacceptable body weight differences between drug treated and control animals (greater than $-4$ grams).

To further evaluate the biological activity of the four isomers of the present invention in comparison with one another and with cisplatin, the complexes are compared in vitro by the biochemical phage induction assay of Sarma, supra. This assay detects a wide variety of compounds which interact with DNA. According to the results presented in FIG. 1, all of the isomers are less effective than cisplatin in inducing prophage. This finding may support the hypothesis that platinum IV complexes are chemically less reactive. However, in vivo there is evidence that platinum IV complexes may be reduced to platinum (II) complexes [Pendyala, L. *Proceedings 13th International Cancer Congress*, Seatle, Wash., #3034, page 531, (1982)]. Therefore, without being bound to any theory it is speculated that the demonstrated in vivo antitumor response illustrated in Tables 2–5 may be a result of the compounds acting either as Platinum II or platinum (IV) complexes or as both types. It is noted that the four isomers are not equal in their ability to induce the prophage. The cis isomer is practically inert and the trans dl isomer is intermediate in effectiveness (about 68 enzyme units). The purified trans d and trans l isomers are the most effective inducers among the four (about 104 enzyme units each); however, the trans d isomer is more potent (optimal effect at 25 $\mu$g/ml for the trans d isomer and at 50 $\mu$g/ml for the trans l isomer).

Thus the isomers possess different water solubilities as well as biological activity as shown in two types of assays: prophage induction assay, and the antitumor experiments. If one summarizes the data in Tables 2–4 by totalling the number of long-term survivors, unexpected differences among the isomers become apparent. For example, the trans l compound produced 30 long-term survivors.

TABLE 2

Dose-Responses Comparisons of Cisplatin, Carboxyphthalato Platinum, and the Four Purified Isomers of Tetrachloro (1,2-diaminocyclohexane) Platinum (IV) Against IP-Implanted L1210 Leukemia

| Name | Dose (Mg/Kg/Dose) | Body Weight Difference (Grams) | Median % T/C | 30-Day Survivors/Total | Approx. Log10 Change in Tumor Burden at End of Rx |
|---|---|---|---|---|---|
| Diluent Control | | | | 0/33 | 3.2 |
| Cisplatin | 20 | −5.0 | 357 | 3/6 | −5.7 |
| | 10 | −1.3 | 166 | 0/6 | 1.9 |
| | 5 | −1.4 | 152 | 0/6 | 2.4 |
| | 2.5 | −1.2 | 134 | 0/6 | 2.7 |
| | 1.25 | −1.0 | 123 | 0/6 | 2.9 |
| Carboxyphthalato Platinum | 50 | −5.0 | 345 | 2/6 | −5.7 |
| | 25 | −1.5 | 357 | 4/6 | −5.7 |
| | 12.5 | −2.1 | 309 | 2/6 | −5.7 |
| | 6.25 | −0.8 | 154 | 0/6 | 2.3 |
| | 3.13 | −0.5 | 146 | 0/6 | 2.5 |

TABLE 2-continued

Dose-Responses Comparisons of Cisplatin, Carboxyphthalato Platinum, and the Four Purified Isomers of Tetrachloro (1,2-diaminocyclohexane) Platinum (IV) Against IP-Implanted L1210 Leukemia

| Name | Dose (Mg/Kg/Dose) | Body Weight Difference (Grams) | Median % T/C | 30-Day Survivors/Total | Approx. Log10 Change in Tumor Burden at End of Rx |
|---|---|---|---|---|---|
| trans (l) | 16 | −3.5 | 119 | 0/6 | 3.0 |
|  | 8 | −2.5 | 319 | 1/6 | −5.7 |
|  | 4 | −1.2 | 238 | 2/6 | −2.8 |
|  | 2 | −0.9 | 170 | 0/6 | 1.7 |
|  | 1 | −0.4 | 134 | 0/6 | 2.7 |
| trans (d, l) | 16 | −4.6 | 142 | 1/6 | 2.6 |
|  | 8 | −1.2 | 357 | 4/6 | −5.7 |
|  | 4 | −1.5 | 202 | 1/6 | −0.5 |
|  | 2 | −1.5 | 146 | 0/6 | 2.5 |
|  | 1 | −0.5 | 122 | 0/6 | 2.9 |
| trans (d) | 16 | −4.9 | 226 | 1/6 | −2.0 |
|  | 8 | −1.7 | 357 | 3/6 | −5.7 |
|  | 4 | −0.9 | 211 | 1/6 | −1.1 |
|  | 2 | −0.6 | 134 | 0/6 | 2.7 |
|  | 1 | −0.3 | 119 | 0/6 | 3.0 |
| Cis | 16 | −3.6 | 333 | 2/6 | −5.7 |
|  | 8 | −1.8 | 205 | 0/6 | −0.7 |
|  | 4 | −1.1 | 152 | 0/6 | 2.4 |
|  | 2 | −1.3 | 140 | 0/6 | 2.6 |
|  | 1 | −0.8 | 128 | 0/6 | 2.8 |

This experiment (A8-00005 3LE31) was conducted at the Southern Research Institute, Birmingham, Ala. under the supervision of Dr. Daniel Griswold. The protocols were the same as those published previously (Geran et al., Cancer Chemotherapy Reports 3: No. 2, 1972 [Attachment 11]). $10^5$ cells were implanted intraperitoneally in CD2F1 male mice on Day 0. Drug treatments were given intraperitoneally as single injections at the doses indicated on Days 1, 5 and 9 after tumor implantation. The diluent was saline except for NSC-271674 where 5% sodium bicarbonate was used. All drugs were prepared fresh on the day of injection, and all were administered in solution. Median survival times for both control and drug-treated mice were determined and expressed as a percentage (% T/C). Body weights were determined on Day 5 and expressed as a weight difference (body weight of the drug-treated animals minus that of the control animals in grams) (T-C). The diluent control animals lived a median of 8.4 days and gained 1.9 grams by Day 5 in this experiment. All animals, including Day 30 survivors, were used in the calculation of median survival times. The $\log_{10}$ change in tumor burden refers to the net log change in viable tumor cell population at the end of therapy (Rx) as compared to the start of therapy; e.g., a −6 log change means that there was a 99.99% reduction and a 3 log change means there was a 1000-fold increase in tumor burden at the end of therapy. The tumor burden at the start of therapy was about $6.1 \times 10^5$ cells in this experiment.

TABLE 3

Activity of Platinum Complexes Against IP-Implanted L1210 Leukemias Sensitive and Resistant to Cisplatin (30 Day Test)

| | | IP L1210 | | | IP L1210/Cisplatin | | |
|---|---|---|---|---|---|---|---|
| Name | Dose (Mg/Kg/Dose) | Median % T/C | 30 Day Survivors/Total | Approx. Log10 Change in Tumor Burden at End of RX | Median % T/C | 30 Day Survivors/Total | Approx. Log10 Change in Tumor Burden at End of RX |
| Diluent Control | — | — | 0/33 | 3.1 | — | 0/33 | 3.1 |
| Cisplatin | 20 | 148 | 0/6 | 2.4 | 86* | 0/6 | |
|  | 10 | 348 | 3/6 | −5.9 | 108 | 0/6 | 2.9 |
|  | 5 | 162 | 0/6 | 2.2 | 101 | 0/6 | 3.1 |
|  | 2.5 | 131 | 0/6 | 2.7 | 106 | 0/6 | 3.0 |
|  | 1.25 | 116 | 0/6 | 3.0 | 104 | 0/6 | 3.0 |
| Carboxyphthalato Platinum | 50 | 50* | 0/6 | | 129* | 1/6 | |
|  | 25 | 73* | 0/6 | | 304 | 2/6 | −5.9 |
|  | 12.5 | 348 | 6/6 | −5.9 | 322 | 4/6 | −5.9 |
|  | 6.25 | 348 | 5/6 | −5.9 | 322 | 4/6 | −5.9 |
|  | 3.13 | 174 | 1/6 | 1.4 | 139 | 2/6 | 2.4 |
| trans (l) | 16 | 93* | 0/6 | | 89 | 0/6 | 3.1 |
|  | 8 | 348 | 4/6 | −5.9 | 322 | 5/6 | −5.9 |
|  | 4 | 313 | 2/6 | −5.9 | 322 | 5/6 | −5.9 |
|  | 2 | 197 | 1/6 | −0.4 | 137 | 0/6 | 2.5 |
|  | 1 | 143* | 0/6 | 2.5 | 118 | 0/6 | 2.8 |
| trans (d, l) | 16 | 143* | 1/6 | | 110* | 1/6 | |
|  | 8 | 348 | 3/6 | −5.9 | 322 | 4/6 | −5.9 |
|  | 4 | 212 | 2/6 | −1.5 | 225 | 2/6 | −3.4 |
|  | 2 | 151 | 0/6 | 2.4 | 118 | 0/6 | 2.8 |
|  | 1 | 125 | 0/6 | 2.8 | 115 | 0/6 | 2.8 |
| trans (d) | 16 | 96* | 0/6 | | 143* | 1/6 | |
|  | 8 | 348 | 3/6 | −5.9 | 322 | 3/6 | −5.9 |
|  | 4 | 209 | 2/6 | −1.2 | 139 | 0/6 | 2.4 |

TABLE 3-continued

Activity of Platinum Complexes Against IP-Implanted L1210 Leukemias Sensitive and Resistant to Cisplatin (30 Day Test)

| | | IP L1210 | | | IP L1210/Cisplatin | | |
|---|---|---|---|---|---|---|---|
| Name | Dose (Mg/Kg/Dose) | Median % T/C | 30 Day Survivors/Total | Approx. Log10 Change in Tumor Burden at End of RX | Median % T/C | 30 Day Survivors/Total | Approx. Log10 Change in Tumor Burden at End of RX |
| | 2 | 144 | 0/6 | 2.5 | 116 | 0/6 | 2.8 |
| | 1 | 113 | 0/6 | 3.0 | 101 | 0/6 | 3.1 |
| Cis | 16 | 267* | 1/6 | −5.7 | 322 | 3/6 | −5.9 |
| | 8 | 325 | 2/6 | −5.9 | 138 | 0/6 | 2.4 |
| | 4 | 148 | 0/6 | 2.4 | 111 | 0/6 | 2.9 |
| | 2 | 139 | 0/6 | 2.6 | 110 | 0/6 | 2.9 |
| | 1 | 125 | 0/6 | 2.8 | 105 | 0/6 | 3.0 |

*Animal weight difference (test - control) ≧ −4.0 grams.

These experiments (A8-00008 3LE31 and A8-00001 3DP31) were conducted concurrently at the Southern Research Institute, Birmingham, Ala. under the supervision of Dr. Daniel Griswold. See Table 4 for experimental details. The diluent control animals bearing L1210 leukemia lived a median of 8.6 days and gained 1.3 grams by Day 5. The corresponding data for animals bearing L1210/Cisplatin were 9.3 days and 0.6 grams. The tumor burden at the start of therapy was about $7.7 \times 10^5$ cells for L1210 and $8.3 \times 10^5$ cells for L1210/Cisplatin. Female CD2F1 mice were used for these experiments.

TABLE 4

Activity of Platinum Complexes Against IP-Implanted L1210 Leukemias Sensitive and Resistant to Cisplatin (60 Day Test)

| | | IP L1210 | | | IP L1210/Cisplatin | | |
|---|---|---|---|---|---|---|---|
| Name | Dose (Mg/Kg/Dose) | Body Weight Difference (Grams) | Median % T/C | 60 Day Survivors/Total | Body Weight Difference (Grams) | Median % T/C | 60 Day Survivors/Total |
| Diluent Control | — | — | — | 0/43 | — | — | 0/43 |
| Cisplatin | 20 | −5.8 | Toxic | 0/10 | −5.6 | Toxic | 0/10 |
| | 10 | −5.1 | 107 | 0/10 | −5.1 | 87 | 0/10 |
| | 5 | −2.4 | 240 | 0/10 | −2.3 | 110 | 0/10 |
| | 2.5 | −1.4 | 154 | 0/10 | −0.3 | 105 | 0/10 |
| | 1.25 | −0.6 | 127 | 0/10 | −0.1 | 103 | 0/10 |
| Carboxyphthalato Platinum | 50 | | Toxic | 0/10 | | Toxic | 0/10 |
| | 25 | | Toxic | 0/10 | −3.7 | Toxic | 0/10 |
| | 12.5 | −6.0 | Toxic | 0/10 | −5.5 | Toxic | 0/10 |
| | 6.25 | −3.5 | 313 | 2/10 | −2.9 | 236 | 2/10 |
| | 3.13 | −2.3 | 280 | 2/10 | −1.2 | 645 | 6/10 |
| trans (l) | 16 | −5.9 | Toxic | 0/10 | −7.3 | Toxic | 0/10 |
| | 8 | −3.7 | 228 | 1/10 | −3.5 | 133 | 0/10 |
| | 4 | −2.2 | 208 | 0/10 | −1.7 | 376 | 3/8 |
| | 2 | −0.8 | 216 | 2/10 | −0.8 | 239 | 4/10 |
| | 1 | −0.4 | 146 | 0/10 | −1.1 | 132 | 0/10 |
| trans (d, l) | 16 | −5.9 | 89 | 0/10 | −6.3 | Toxic | 0/10 |
| | 8 | −3.2 | 178 | 3/10 | −4.0 | 236 | 0/10 |
| | 4 | −1.5 | 274 | 0/10 | −1.2 | 451 | 4/10 |
| | 2 | −1.2 | 180 | 0/10 | −0.8 | 139 | 1/10 |
| | 1 | −0.8 | 144 | 0/10 | −0.6 | 129 | 0/10 |
| trans (d) | 16 | −7.0 | Toxic | 0/10 | −6.1 | Toxic | 0/10 |
| | 8 | −3.1 | 301 | 3/10 | −4.8 | 193 | 1/10 |
| | 4 | −1.2 | 202 | 0/10 | −1.4 | 645 | 6/10 |
| | 2 | −1.0 | 216 | 3/10 | −0.2 | 147 | 0/10 |
| | 1 | −0.6 | 144 | 0/10 | −0.4 | 125 | 0/10 |
| Cis | 32 | −5.6 | Toxic | 0/10 | −5.1 | Toxic | 0/10 |
| | 16 | −5.6 | 98 | 0/10 | −5.4 | Toxic | 0/10 |
| | 8 | −2.3 | 313 | 2/10 | −2.7 | 191 | 1/10 |
| | 4 | −0.9 | 250 | 2/10 | 0.0 | 130 | 0/10 |
| | 2 | −0.9 | 143 | 0/10 | −0.3 | 121 | 0/10 |

These experiments (23-00081 3LE31 and 23-00003 3DP31) were conducted concurrently at the Mason Research Institute, Worcester, MA under the supervision of Dr. William Cobb. See Table 4 for experimental details. The diluent control animals bearing L1210 leukemia lived a median of 8.3 days and gained 1.6 grams by Day 5. The corresponding data for animals bearing L1210/Cisplatin were 9.3 days and 1.3 grams. Female CD2F1 mice were used for these experiments.

TABLE 5

Activity of Platinum Complexes Against the SC Implanted L1210 Leukemia Following Intravenous Administration

| Name | Dose Range (mg/kg/inj) | Optimal Dose (mg/kg/inj) | Body Weight Difference (Grams) | Median Survival Time (Days) | Median % T/C |
|---|---|---|---|---|---|
| Diluent Control | — | — | — | 10.3 | — |

TABLE 5-continued

Activity of Platinum Complexes Against the SC Implanted
L1210 Leukemia Following Intravenous Administration

| Name | Dose Range (mg/kg/inj) | Optimal Dose (mg/kg/inj) | | Body Weight Difference (Grams) | Median Survival Time (Days) | Median % T/C |
|---|---|---|---|---|---|---|
| Cisplatin | 10–1.25 | | 5 | −5.7 | 14.3 | 138 |
| | | HNTD* | 2.5 | −2.8 | 11.8 | 114 |
| Carboxyphthalato Platinum | 12.5–0.78 | | 12.5 | −6.1 | 17.0 | 165 |
| | | HNTD* | 6.25 | −2.6 | 12.8 | 124 |
| trans (l) | 10.0–0.63 | | 2.5 | −2.3 | 15.0 | 145 |
| trans (d, l) | 10.0–0.63 | | 2.5 | −2.6 | 13.8 | 133 |
| trans (d) | 10.0–0.63 | | 5.0 | −6.4 | 17.8 | 172 |
| | | HNTD* | 2.5 | −1.5 | 13.0 | 126 |
| Cis | 10.0–0.63 | | 5.0 | −3.3 | 13.7 | 133 |

*HNTD refers to the "highest non-toxic dose," which in this experiment refers to a dose producing an animal weight difference (test-control) ≧ −4.0 grams.

This experiment (A8-00004 3LE32) was conducted at the Southern Research Institute, Birmingham, Ala. under the supervision of Dr. Daniel Griswold. The protocols were the same as those published previously (Attachment 11). $10^6$ cells were implanted subcutaneously in CD2Fl male mice on Day 0. Drug treatments were given intravenously once daily at the doses indicated on Days 1–5 after tumor implantation. The dosage range tested included the highest and lowest doses indicated in the Table as well as intermediate values which were determined by multiplying each dose in turn by 0.5 starting with the highest dose. The diluent was saline except for NSC-271674 for which 5% sodium bicarbonate was used. All drugs were prepared fresh on the day of injection, and all were administered in solution. Median survival times for both control and drug-treated mice were determined and expressed as a percentage (% T/C). Body weights were determined on Day 5 and expressed as a weight difference (body weight of the drug-treated animals minus that of the control animals in grams) (T-C). The diluent control animals lived a median of 10.3 days and gained 0.5 grams by Day 5 in this experiment.

TABLE 6

Comparison of the Four Purified Isomers of Tetrachloro (1,2 diaminocyclohexane) Platinum (IV) in Regard to Long Term Survivors and Weight Differences in Treating IP-Implanted L1210/Cisplatin

| Compound | Total Number of Long-Term Survivors | Total Grams of Weight Difference | Ratio of 2/1 |
|---|---|---|---|
| trans (l) | 17 | −6.0 | 0.35 |
| trans (d, l) | 12 | −10.0 | 0.80 |
| trans (d) | 11 | −11.9 | 1.08 |
| Cis | 4 | −5.6 | 1.40 |

TABLE 7

Comparative Solubilities of Platinum Complexes

| Compound | Water Solubility (mg/L) | Mouse Optimal* Dose (mg/kg) | Water Solubility mg/L Mouse Optimal* Dose (mg/kg) |
|---|---|---|---|
| Cisplatin | 1,000 | 10 | 100 |
| Carboxyphthalato platinum | 20,000** | 12.5 | 1,600 |
| trans (l) | 15,000 | 8 | 1,875 |
| trans (d, l) | 6,000 | 8 | 750 |
| trans (d) | 15,000 | 8 | 1,875 |
| Cis | 2,000 | 8 | 250 |

*IP L1210 leukemia, Days 1, 5 and 9 schedule. Highest tolerated dose in at least 2 of 3 experiments (i.e,. animal weight difference (test-control) ≦ −4 grams by Day 5).
**0.1 M NaHCO$_3$ Comparative data for the others are as follows: 27 for trans d, 27 for trans d l and 13 for cis. It one compares the number of long-term survivors and the weight differences observed in treating the IP-implanted L1210/cisplatin, the trans l isomer appears to produce more long-term survivors and also to be the least toxic (Table 6). All of the evidence taken together indicates that the cis isomer, a component of the mixture prepared by Schwartz, et al., supra, has relatively lower biological activity. Therefore, the effort to prepare purified isomers has produced unexpected results, i.e. products with superior biological and chemical properties when compared with the material prepared by Schwartz, et al. (NSC-276017). Table 6 further shows that by preparing the four isomers and comparing their optimal doses and solubilities, compounds with vastly better dose to solubility ratios are produced as compared to the cis isomer, which is similar to the material prepared by Schwartz et al. This ratio is important in determining the dosage volume required for both conventional and high dose therapy in patients. The higher the ratio the more convenient it is to prepare a formulation for intravenous administration to patients which is shown in Table 7.

Having described several embodiments of a new and improved organo-platinum (IV) complex and their new and improved properties, it is believed that other modifications, variations and changes will be suggested to those of ordinary skill in the art in light of the disclosure herein. It is, therefore, to be understood that all such variations, modifications and changes are included within the scope and purview of this invention as defined herein by the appended claims.

What is claimed is:

1. A substantially isomerically pure tetrahalo (1,2-diaminocyclohexane) platinum (IV) complex of the following formula:

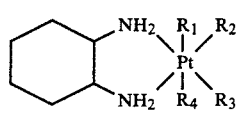

wherein $R_1$ $R_2$ $R_3$ and $R_4$ are the same or different substitutents selected from the group consisting of chlorine, bromine, iodine and fluorine.

2. The complex of claim 1 wherein said tetrahalo complex is a tetrachloro complex.

3. The complex of claim 2 selected from the group consisting of trans d, trans l, trans d,l, and cis isomers thereof.

4. The complex of claim 3 being greater than 99% pure.

5. An antineoplastic composition consisting essentially of as an active ingredient an antineoplastically effective amount of a substantially isomerically pure tetrahalo (1,2-diaminocyclohexane) platinum (IV) complex of the following formula:

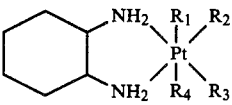

wherein $R_1$ $R_2$ $R_3$ and $R_4$ are the same or different substitutents selected from the group consisting of chlorine, bromine, iodine and fluorine; and physiologically acceptable carrier or adjuvant.

6. The composition of claim 5 wherein said tetrahalo complex is a tetrachloro complex.

7. The composition of claim 6 wherein said complex is selected from the group consisting of trans d, trans l, trans d,l, and cis isomers thereof.

8. The composition of claim 7 wherein the amount of the active ingredient ranges from about 1.0 to 200 mg/m².

9. The composition of claim 8 wherein said complex is greater than 99% pure.

10. The complex of claim 2 being trans d, trans l or trans d,l isomer.

11. The complex of claim 10 being greater than 99% pure.

12. The composition of claim 6 being trans d, trans l or trans d,l isomer.

13. The composition of claim 12 being greater than 99% pure.

* * * * *